United States Patent [19]
Russell

[11] Patent Number: 5,383,233
[45] Date of Patent: Jan. 17, 1995

[54] METHOD FOR IDENTIFYING ARTIFACTUAL RADIOGRAPHIC IMAGES CAUSED BY EPITHELIAL PROTUBERANCES

[75] Inventor: Donald G. Russell, Kensington, Conn.

[73] Assignee: Beekly Corporation, Bristol, Conn.

[21] Appl. No.: 59,201

[22] Filed: May 7, 1993

[51] Int. Cl.⁶ .............................................. H05G 1/28
[52] U.S. Cl. ...................................... 378/162; 378/37
[58] Field of Search .......................... 378/162, 163, 37

[56] References Cited
U.S. PATENT DOCUMENTS
4,506,676 3/1985 Duska ................................. 378/162

Primary Examiner—Craig E. Church
Attorney, Agent, or Firm—McCormick, Paulding & Huber

[57] ABSTRACT

The present invention provides a method for identifying the artifactual radiographic images caused by epithelial protuberances. The claimed method employs a partially radiolucent, faintly radiopaque marker which is secured around an epithelial protuberance. The marker is designed so that when secured it not only preserves the generally cylindrical shape and vertical boundaries of the protuberance, but also ensures that a thin layer or film of air is maintained surrounding the protuberance. After the marker is secured, the preserved vertical boundaries of the protuberance are presented tangentially to an xray beam to produce a radiographic shadow of both the protuberance and the marker. The artifactual radiographic image caused by the protuberance can then be readily identified by detecting the radiographic shadow cast by the protuberance in association with the shadow cast by the surrounding, faintly opaque marker.

8 Claims, 6 Drawing Sheets

METHOD FOR IDENTIFYING ARTIFACTUAL RADIOGRAPHIC IMAGES CAUSED BY EPITHELIAL PROTUBERANCES

BACKGROUND OF THE INVENTION

The present invention relates generally to radiographic imaging and, more particularly, to a method for reliably identifying the artifactual images caused my epithelial protuberances.

It is well established that common epithelial protuberances can be the source of confusing artifactual radiographic images. There are, for example, textbook descriptions of a nipple shadow appearing to be a lung nodule. In mammography, nevi, papillomas and other projecting epithelial structures may appear to be soft tissue masses within the breast parenchyma.

It is also well known to those skilled in the art of chest radiography to tape a radiopaque lead marker to a protuberant nipple to identify the spurious shadow cast by the nipple as an artifact. Mammographers have also suggested the use of a similar marker to identify artifactual images caused by skin nevi and papillomas. The principal drawback with such a practice, however, is that while the marker is routinely imaged, the shadow of the protuberance may or may not be seen. This is due primarily to the fragile, soft, deformable nature of epithelial protuberances and the unpredictable manner in which they will create an image. For example, taping a lead marker over a nevus or nipple often displaces air from around the object and distorts its generally cylindrical shape. In such cases, the protuberance is flattened and there is a low probability that the object will be imaged.

Accordingly, it is an object of the present invention to provide a method which ensures that an epithelial protuberance will consistently generate a well defined radiographic image during a mammography, chest radiography or other radiographic procedure.

It is a further object of the invention to provide such a method wherein the radiographic image caused by the protuberance can be reliably identified as an artifactual image.

SUMMARY OF THE INVENTION

The present invention meets these and other objects by providing a method wherein a partially radiolucent, faintly radiopaque marker is secured around an epithelial protuberance. The marker is designed so that when secured it not only preserves the generally cylindrical shape and vertical boundaries of the protuberance, but also ensures that a thin layer or film of air is maintained surrounding the protuberance. After the marker is secured, the preserved vertical boundaries of the protuberance are presented tangentially to an xray beam to produce a radiographic shadow of both the protuberance and the marker. Finally, the artifactual radiographic image caused by the protuberance is readily identified by detecting the radiographic shadow cast by the protuberance in association with the shadow cast by the surrounding faintly opaque marker. In one preferred embodiment of the invention, the marker is a generally ring-shaped, partially radiolucent, faintly radiopaque collar secured around the protuberance.

DETAILED DESCRIPTION OF THE INVENTION

Nipples, nevi and similar epithelial protuberances are soft tissue cylinders having a radiographic density approximately equal to that of water. These soft tissue cylinders project vertically from the surface of the skin into the surrounding air, and if such structures are not compressed or mechanically deformed in some other manner they will radiographically exhibit a well defined shadow with sharp image margins. The difference between the absorption of xrays in air versus soft tissue is approximately 1:10,000. This enormous difference in xray absorption results in a sharp, vivid radiographic image when the vertical boundaries of a protuberance are presented tangentially to an xray beam.

The present invention is directed to a method which exploits these natural imaging characteristics of skin protuberances. The method employs a partially radiolucent, faintly radiopaque marker, i.e., a marker having a low to intermediate radiographic density, which is secured surrounding a protuberance in a manner which preserves the cylindrical shape and the vertical boundaries of the protuberance. Unlike prior art radiographic methods which utilize markers taped or otherwise affixed to a protuberance, the marker of the present invention does not compress, flatten or otherwise distort the cylindrical shape of epithelial protuberances; accordingly, such protuberances can then be consistently imaged and reliably identified.

Depending on the particular protuberance to be imaged, markers of various shapes can be used such as, for example, ring-shaped, oval-shaped, square-shaped or triangular-shaped markers. However, and without limiting the invention in this regard, the detailed description of the invention relates to the O-shaped collar illustrated in the accompanying FIGS.

Figure 1:
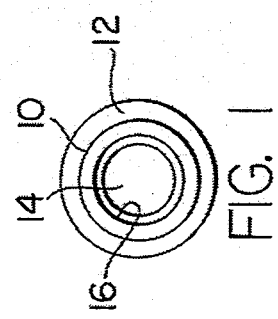
FIG. 1 is a plan view of a rubber collar useful in practicing the method of the present invention.

Referring now to FIG. 1, a rubber O-shaped collar or ring 10 is secured around a protuberance to be imaged and identified. The collar 10 is adhered to or otherwise mounted on an adhesive backing 12 which permits the collar to be securely attached to the surface of a patient's skin. O-shaped collars having a thickness of from about 1.5 mm to about 2 mm and a central opening 14 of from about 12 mm to about 15 mm are appropriate as nipple markers in chest radiography. For mammography, smaller, thinner rings with a central opening of from about 10 mm to about 12 mm and a thickness of from about 1 mm to about 2 mm are effective. As long as a thin layer or film of air is maintained between the inside surface 16 of collar and the protuberance which the collar surrounds, there is considerable latitude as to the diameter of the internal opening and the thickness of the particular collar chosen.

As noted previously, the collar 10 is formed from partially radiolucent rubber, plastic, aluminum or other suitable substances. It is important that the collars be formed from the highest quality material and that the material have sufficient radiolucency to permit imaging of fine tissue detail and small calcium deposits that might be present in the tissue underlying the collar.

Figure 2:
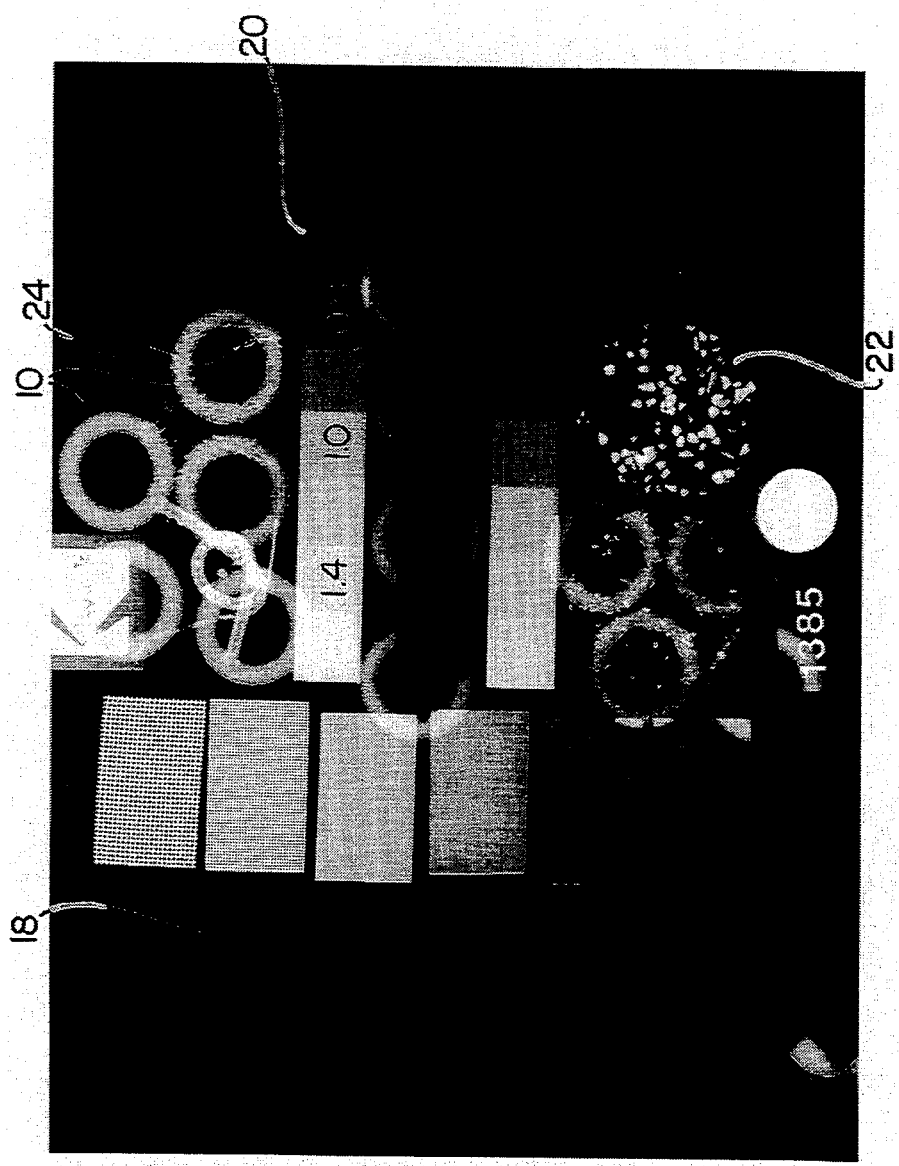
FIG. 2 is a radiographic image of several of the collars shown in FIG. 1 radiographed on the surface of a mammography phantom.

FIG. 2 shows a number of the collars 10 radiographed on the surface of a Kodak mammography phantom 18. The exposure is at 28KV, and the collars are equivalent to 1.2 mm of aluminum. This is established by the aluminum step wedge 20 shown in FIG. 2 which is graduated in 0.2 mm increments as the annotations indicate. As further illustrated in FIG. 2, the simulated micro calcifications 22 and fine tissue details 24 are clearly imaged through the collars.

Figure 3:
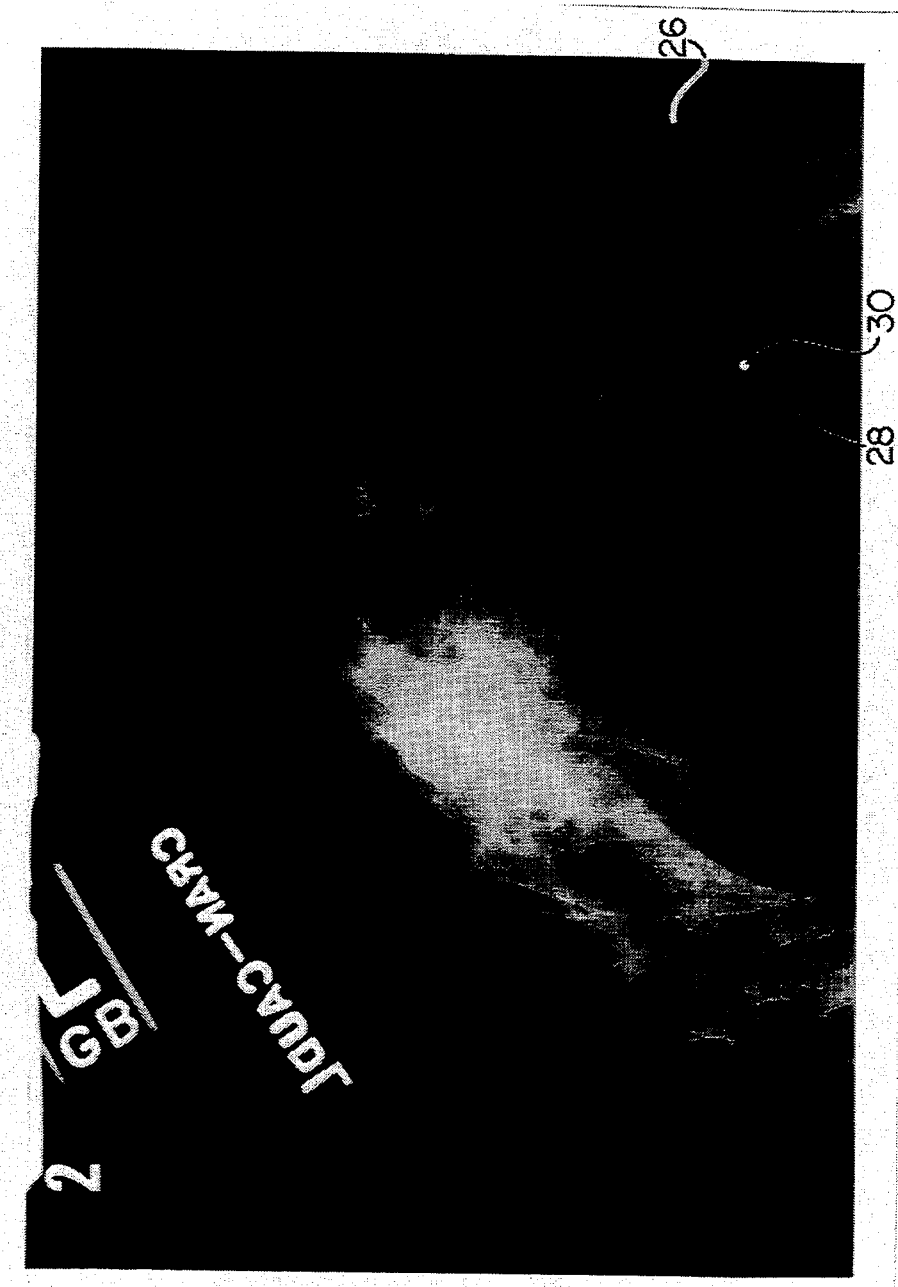
FIG. 3 is a cranio-caudal view of a patient's left breast having a skin nevus on the upper medial aspect thereof marked with a prior art lead marker taped over the nevus.
Figure 4:
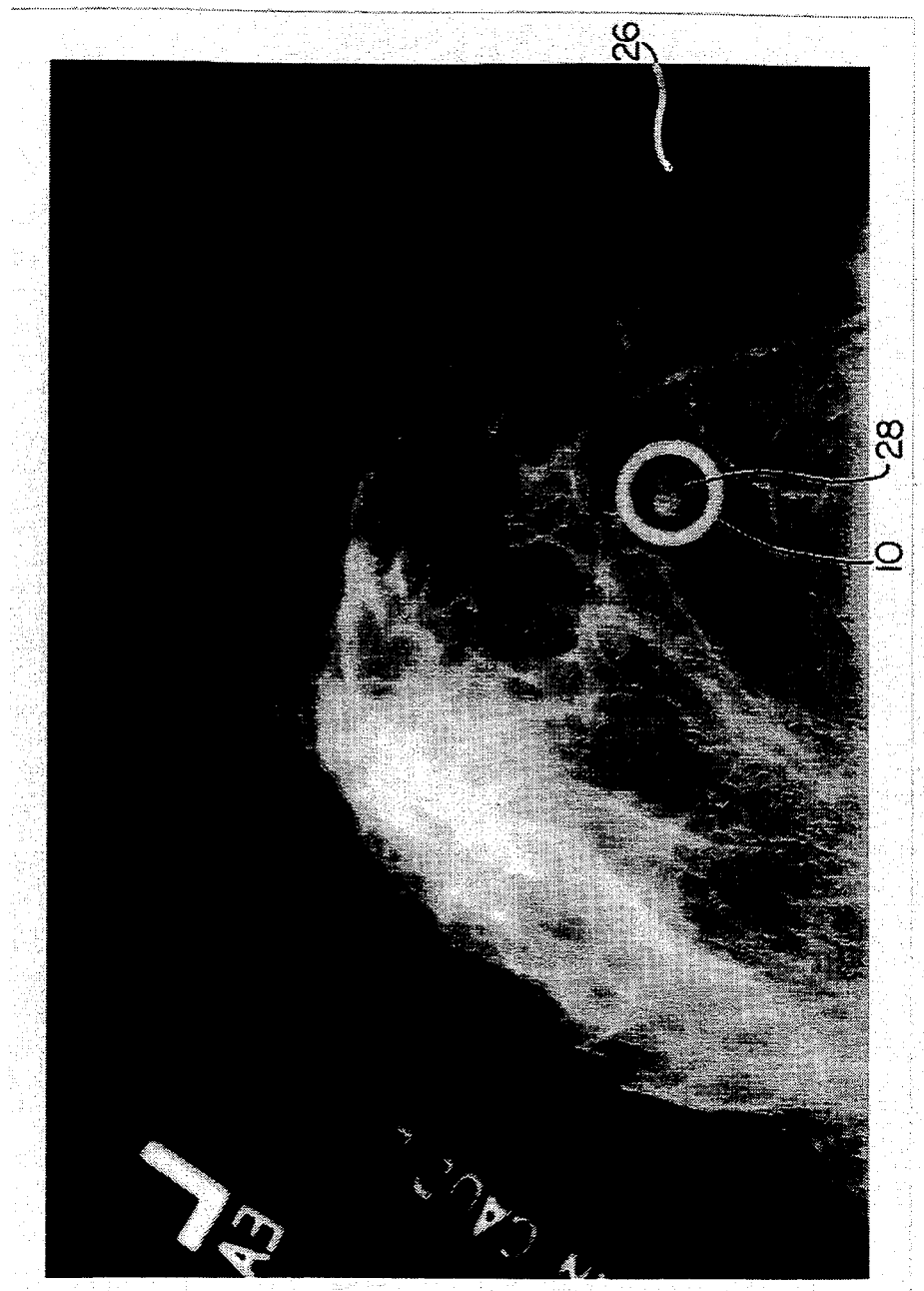
FIG. 4 is a radiographic image of the nevus of FIG. 3 marked with the collar shown in FIG. 1.

FIG. 3 is a cranio caudal view taken in 1987 of the left breast 26 of a patient having an elevated skin nevus 28 on the upper medial aspect of the breast. The nevus is marked with a prior art small lead marker 30. FIG. 4 illustrates the same view of the patient's breast taken during a follow up examination three years later. In this examination, the nevus 28 was marked with the collar 10. Taken together, FIGS. 3 and 4 clearly indicate the advantages of the present invention over the prior art method of taping or otherwise attaching a lead marker over a nevus. Whereas in FIG. 3 the nevus 28 is barely distinguishable from the surrounding breast tissue, FIG. 4 shows the image of the nevus clearly and conclusively identified within the shadow of the collar 10.

Figure 5:
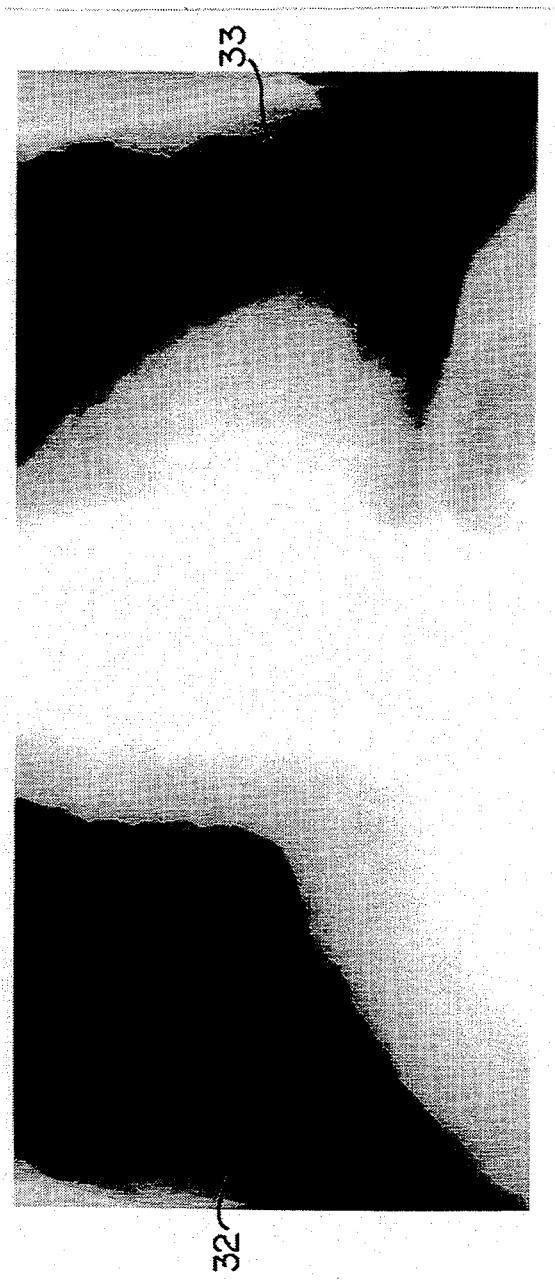
FIG. 5 is the chest film of a male having a soft tissue shadow in each lower lung field.
Figure 6:
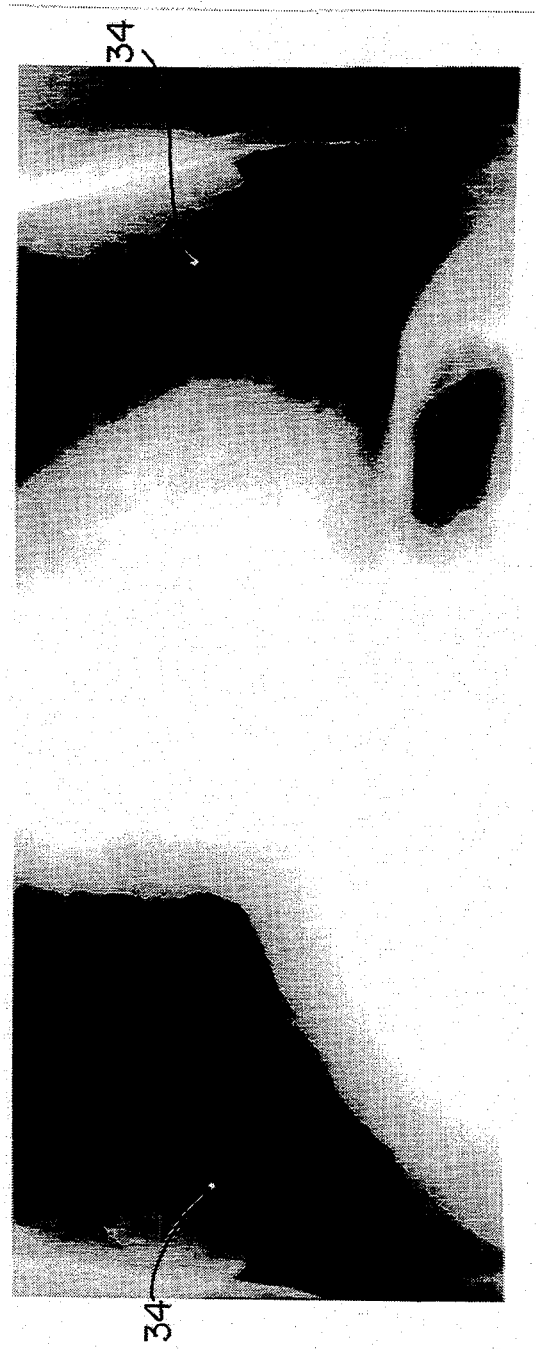
FIG. 6 is a second chest film of the male of FIG. 5 with a prior art lead marker taped to each nipple.
Figure 7:
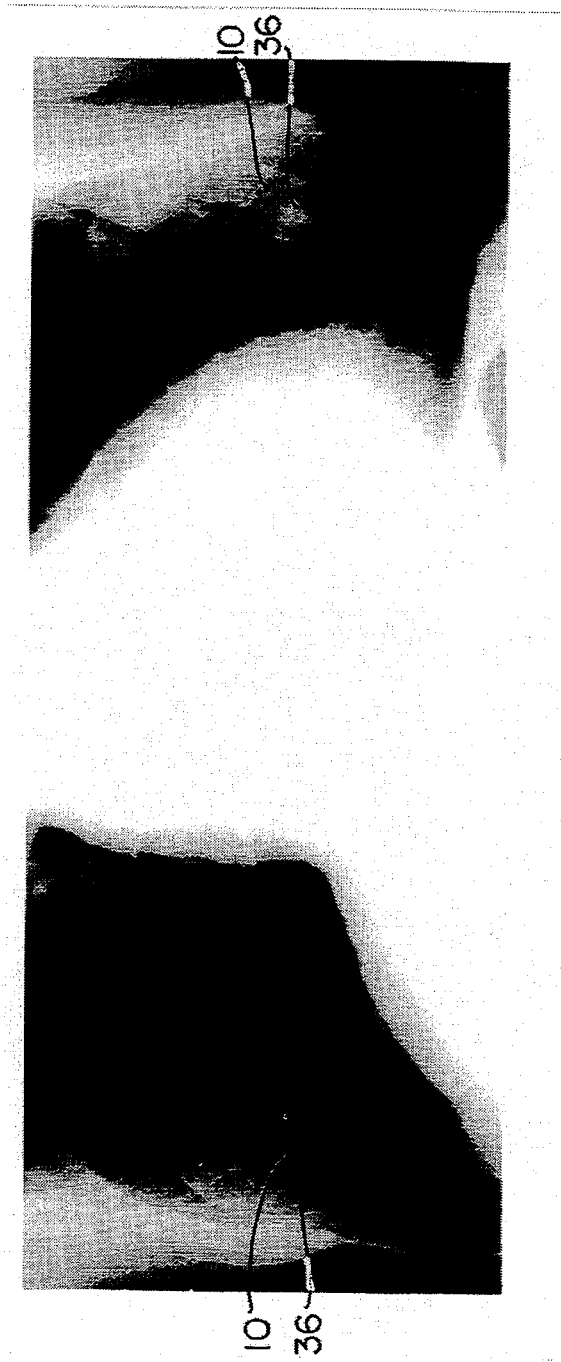
FIG. 7 is a third chest film of the male of FIG. 5 with each nipple marked with the collar shown in FIG. 1.

The advantages of the present invention over the prior art are further illustrated by FIGS. 5-7. FIG. 5 is the chest film of an elderly male admitted with bowel carcinoma. There is a small, soft tissue, round shadow 33, 32 in each lower lung field. The chest film was repeated with a small lead marker 34, 34 taped on top of each of the patient's nipples. In this film, as shown in FIG. 6, the markers are evident without any evidence of the shadows 32, 33. FIG. 7 illustrates a third chest film of the same patient. This time a collar 10 was placed around each of the patient's nipples 36, 37. Now, the nipples, protected by the collars, are clearly identified as source of the artifactual images or shadows 32, 33.

To further substantiate the advantages of the present invention over prior art methods of radiography, a series of 51 mammography patients were retrospectively reviewed. There was a total of 66 nevi or papillomas marked with an O-shaped collar, In 59 of these cases (89%), the image of the nevus was clearly seen within the shadow of the collar on one or more of the views. Of these 59 nevi, 27 were found which had previously been marked with an opaque lead marker; in only 3 cases (11%) was the shadow of the nevus discernible under the opaque marker. Furthermore, a review of earlier mammograms of these patients revealed 26 nevi not marked in any manner; again only 4 (15%) did cast an artifactual shadow.

In a smaller series in chest radiography, nineteen patients, 15 men and 4 women, who had a chest film showing at least one suspected nipple shadow were reviewed. All hat repeat chest films with an O-shaped collar secured around both nipples. In 17 cases (90%) both nipples were imaged within the shadow of the collar. In the remaining two cases, the nipple suspected of casting a shadow was imaged within the collar.

In addition to their application in the above-described method, the collars taught by the present invention are also useful as surface markers in CAT scan procedures. The low to medium radiographic density of the collars makes them ideal for identifying the sites of clinically palpable masses which often are the subject of such procedures. Further, the collars are useful as markers for identifying foreign bodies that may be lodged below the surface of the skin in puncture wounds. In this application, the markers are placed on the surface of the skin surrounding the wound. Thus, any foreign bodies, such as glass particles, that may be lodged within the wound are not obscured as is often the case with prior art lead markers which must be placed over the wound.

While preferred embodiments have been shown and described, various modifications and substitutions may be made without departing from the spirit and scope of the invention. Accordingly, it is to be understood that the present invention has been described by way of example and not by limitation.

I claim:

1. A method for identifying the artifactual radiographic images caused by an epithelial protuberance, said method comprising the steps of:
   securing around the protuberance a partially radiolucent, faintly radiopaque marker adapted to preserve the generally cylindrical shape and vertical boundaries of the protuberance when secured thereto and to maintain a layer of air around the protuberance;
   presenting the vertical boundaries of the protuberance with the marker secured thereto tangentially to an xray beam to produce a radiographic shadow of the protuberance, and
   identifying the artifactual radiographic image caused by the protuberance by detecting the radiographic shadow cast by the protuberance in association with the shadow cast by the surrounding marker.

2. The method of claim 1 wherein the step of securing a radiolucent marker is further characterized in that the marker is a generally ring-shaped collar secured around the protuberance.

3. The method of claim 2 wherein the radiolucent collar is an O-shaped ring.

4. The method of claim 1 wherein the collar is formed from a partially radiolucent, faintly radiopaque material selected from the group consisting of rubber, plastic and aluminum.

5. The method of claim 4 wherein the partially radiolucent, faintly radiopaque material is rubber.

6. The method of claim 1 wherein the marker has sufficient radiolucency to permit imaging of fine tissue detail and micro calcific deposits present in tissue underlying the marker.

7. A method for producing a radiographic image of an epithelial protuberance, said method comprising the steps of:
   securing around the protuberance a partially radiolucent, faintly radiopaque marker adapted to preserve the generally cylindrical shape and vertical boundaries of the protuberance when secured thereto and to maintain a layer of air around the protuberance;
   presenting the vertical boundaries of the protuberance with the marker secured thereto tangentially to an xray beam to produce a radiographic shadow of the protuberance in association with the shadow cast by the surrounding marker.

8. A method for identifying palpable masses and foreign bodies lodged within puncture wounds, said method comprising the steps of:

secured around the wound or the mass a partially radiolucent, faintly radiopaque marker adapted to be secured without obstructing the wound or mass;

presenting the wound or mass with the marker secured thereto to an xray beam to produce a radiographic shadow of the wound or mass, and identifying the radiographic image caused by the mass or the foreign body lodged within the wound by detecting the radiographic shadow cast by the mass or body in association with the shadow cast by the surrounding marker.

* * * * *